United States Patent
Kumar et al.

(10) Patent No.: US 12,026,886 B2
(45) Date of Patent: Jul. 2, 2024

(54) METHOD AND SYSTEM FOR AUTOMATICALLY ESTIMATING A HEPATORENAL INDEX FROM ULTRASOUND IMAGES

(71) Applicants: GE Precision Healthcare LLC, Wauwatosa, WI (US); The General Hospital Corporation, Boston, MA (US)

(72) Inventors: Viksit Kumar, Quincy, MA (US); Anthony E. Samir, Newton, MA (US); Shuhang Wang, Newton, MA (US); Szu-Yeu Hu, Cambridge, MA (US); Paul O'Dea, Muskego, WI (US); Yelena Tsymbalenko, Mequon, WI (US); Michael Washburn, Brookfield, WI (US)

(73) Assignees: THE GENERAL HOSPITAL CORPORATION, Boston, MA (US); GE PRECISION HEALTHCARE LLC, Waukesha, WI (US)

( * ) Notice: Subject to any disclaimer, the term of this patent is extended or adjusted under 35 U.S.C. 154(b) by 362 days.

(21) Appl. No.: 17/155,384

(22) Filed: Jan. 22, 2021

(65) Prior Publication Data
US 2022/0237798 A1   Jul. 28, 2022

(51) Int. Cl.
  *G06K 9/00* (2022.01)
  *A61B 8/00* (2006.01)
  (Continued)

(52) U.S. Cl.
  CPC ............ *G06T 7/11* (2017.01); *A61B 8/08* (2013.01); *A61B 8/461* (2013.01);
  (Continued)

(58) Field of Classification Search
  CPC ............ G06T 7/11; G06T 2207/10016; G06T 2207/10132; G06T 2207/30056;
  (Continued)

(56) References Cited

U.S. PATENT DOCUMENTS

| 2017/0273667 A1 | 9/2017 | Labyed |
| 2019/0200962 A1 | 7/2019 | Lee et al. |
| 2020/0367853 A1 * | 11/2020 | Yoo ........................ G16H 70/20 |

FOREIGN PATENT DOCUMENTS

WO    WO-2020020809 A1 *  1/2020  ............. A61B 8/085

OTHER PUBLICATIONS

Webb, Muriel et al., "Diagnostic Value of a Computerized Hepatorenal Index for Sonographic Quantification of Liver Steatosis," Gastrointestinal Imaging, vol. AJR:192, Apr. 2009, pp. 909-921.
(Continued)

*Primary Examiner* — Alex Kok S Liew
(74) *Attorney, Agent, or Firm* — McAndrews, Held & Malloy, Ltd.; Daniel Bissing; David Bates (57) ABSTRACT

A system and method for automatically estimating a hepatorenal index (HRI) from ultrasound images s provided. The method includes acquiring a sequence of ultrasound image data until a desired ultrasound image view is obtained. The method includes segmenting, a liver and a renal cortex in the obtained ultrasound image view. The method includes identifying valid samples in the liver and the renal cortex in the obtained ultrasound image view by excluding invalid samples. The method includes automatically positioning a liver region of interest and a renal cortex region of interest in the obtained ultrasound image view based on the valid samples and at least one criterion. The method includes determining an HRI and causing a display system to present the HRI.

18 Claims, 5 Drawing Sheets

(51) Int. Cl.
  *A61B 8/08* (2006.01)
  *G06T 7/11* (2017.01)
(52) U.S. Cl.
  CPC ............... *G06T 2207/10016* (2013.01); *G06T 2207/10132* (2013.01); *G06T 2207/30056* (2013.01); *G06T 2207/30084* (2013.01)
(58) Field of Classification Search
  CPC . G06T 2207/30084; G06T 2207/10004; G06T 2207/10136; G06T 2207/20081; G06T 7/0012; G06T 7/12; A61B 8/08; A61B 8/461; A61B 8/5223; A61B 8/5215
  See application file for complete search history.

(56) References Cited

OTHER PUBLICATIONS

Marshall, Richard H. et al., "Hepatorenal Index as an Accurate, Simple, and Effective Tool in Screening for Steatosis," Gastronintestinal Imaging, vol. AJR:199, Nov. 2012, pp. 997-1004.

Ferreira De Almeida E Borges, Valeria et al., "Sonographic Hepatorenal Ratio: A Noninvasive Method to Diagnose Nonalcoholic Steatosis," Journal of Clinical Ultrasound, vol. 41, No. 1, Jan. 2013, pp. 18-25.

Chauhan, Anil et al., "Diagnostic Accuracy of Hepatorenal Index in the Detection and Grading of Hepatic Steatosis," Journal of Clinical Ultrasound, vol. 00, No. 00, 2016, pp. 1-7.

Hilde Loland Von Volkmann et al., "Quantitative measurement of ultrasound attenuation and Hepato-Renal Index in Non-Alcoholic Fatty Liver Disease," Medical Ultrasonography 2013, vol. 15, No. 1, pp. 16-22.

Shiralkar, Kaustubh et al., "Improved Method for Calculating Hepatic Steatosis Using the Hepatorenal Index," Journal of Ultrasound in Medicine 2015, vol. 34, pp. 1051-1059.

Martin-Rodriguez, Jose L. et al., "Sonographic quantification of a Hepato-Renal Index for the assessment of hepatic steatosis in comparison with 3T proton magnetic resonance spectroscopy," European Journal of Gastroenterology & Hepatology 2014, vol. 26, No. 1, pp. 88-94.

Kim, Kwang Baek et al., "Quantification of Hepatorenal Index for Computer-Aided Fatty Liver Classification with Self-Organizing Map and Fuzzy Stretching from Ultrasonography," BioMed Research International, vol. 2015, Article ID 535894, http://dx.doi.org/10.1155/2015/535894, 10 pages.

Soder, Richardo Bernardi et al., "Computer-Assisted Ultrasound Analysis of Liver Echogenicity in Obese and Normal-Weight Children," Pediatric Imaging, vol. AJR:192, May 2009, pp. W201-W206.

* cited by examiner

METHOD AND SYSTEM FOR AUTOMATICALLY ESTIMATING A HEPATORENAL INDEX FROM ULTRASOUND IMAGES

FIELD

Certain embodiments relate to ultrasound imaging. More specifically, certain embodiments relate to a method and system for automatically estimating a hepatorenal index (HRI) from ultrasound images.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a valuable, non-invasive tool for diagnosing various medical conditions, such as non-alcoholic fatty liver disease (NAFLD). NAFLD is one of the most common causes of liver disease in the United States with 30-40% of adults in the United States having NAFLD. Liver with steatosis (i.e., fat content of more than 5%) may be visualized in ultrasound as being brighter than the neighboring kidney. Hepatorenal index (HRI), defined as the ratio of mean sample value of the liver to renal cortex, is a biomarker used in clinical practice for steatosis grading of NAFLD and is a simple and efficient way of identifying liver steatosis. However, clinicians have high subjectivity in estimating HRI due to lack of guidelines and consensus in the community. In addition, identifying liver and kidney region for calculating HRI is subjective to clinician's skill level, size of the region, anatomical view, depth, ultrasound machine, type of input data, and selection/avoidance of certain anatomical parts. For example, a smaller region of interest (ROI) size often used by clinicians makes HRI very susceptible to variations in kidney anatomy.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically estimating a hepatorenal index (HRI) from ultrasound images, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for automatically estimating a hepatorenal index (HRI) from ultrasound images. Various embodiments have the technical effect of automatically calculating HRI from ultrasound images of Morison's pouch view. Certain embodiments have the technical effect of automatically identifying liver and kidney anatomy in the ultrasound image views. Aspects of the present disclosure provide the technical effect of identifying valid samples in the liver and kidney region that may be used for HRI calculation. Various embodiments have the technical effect of identifying an appropriate anatomical view for HRI calculation, calculating an HRI score, and providing a confidence score for each HRI calculation. Certain embodiments have the technical effect of automatically positioning a liver region of interest and a renal cortex region of interest based on identified valid samples. Aspects of the present disclosure have the technical effect of an automated HRI calculation that is objective, user independent, accurate, and optimizes the clinical protocol.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
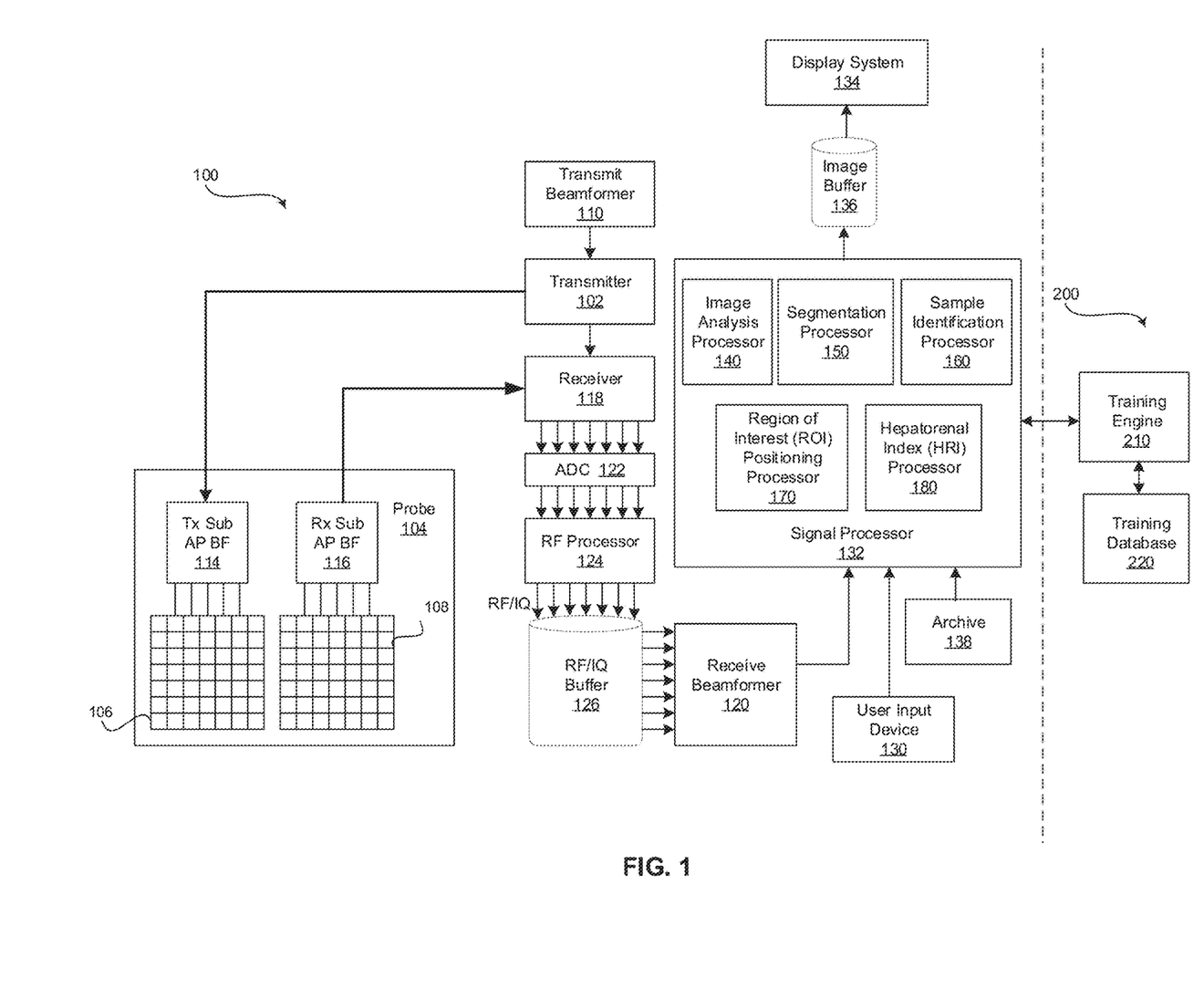
FIG. 1 is a block diagram of an exemplary ultrasound system that is operable to automatically estimate a hepatorenal index (HRI) from ultrasound images, in accordance with various embodiments.

FIG. 1 is a block diagram of an exemplary ultrasound system 100 that is operable to automatically estimate a hepatorenal index (HRI) from ultrasound images, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a liver and a kidney, or any suitable anatomical structure(s).

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select an examination type, select a desired ultrasound image view, select valid sample identification algorithms, reposition automatically-placed regions of interest, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, a touch pad, a trackball, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), an enterprise archive (EA), a vendor-neutral archive (VNA), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an image analysis processor 140, a segmentation processor 150, a sample identification processor 160, a region of interest (ROI) positioning processor 170, and a hepatorenal index (HRI) processor 180. The signal processor 132 may be capable of receiving input information from a user input device 130 and/or archive 138, receiving image data, generating an output displayable by a display system 134, and manipulating the output in response to input information from a user input device 130, among other things. The signal processor 132, including the image analysis processor 140, the segmentation processor 150, the sample identification processor 160, the region of interest (ROI) positioning processor 170, and the hepatorenal index (HRI) processor 180, may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image analysis processor 140 that comprises suitable logic, circuitry, interfaces and/or code that may be operable to analyze acquired ultrasound image data to determine whether a desired ultrasound image view has been obtained. For example, the image analysis processor 140 may analyze ultrasound image data acquired by an ultrasound probe 104 to determine whether a desired view, such as a Morison's pouch ultrasound image view or any suitable ultrasound image view of the liver and kidney, has been obtained. The image analysis processor 140 may direct the signal processor 132 to freeze the view presented at the display system 134 once the desired image view is obtained. The view may be stored at archive 138 and/or any suitable data storage medium. The image analysis processor 140 may include, for example, artificial intelligence image analysis algorithms, one or more deep neural networks (e.g., a convolutional neural network such as u-net) and/or may utilize any suitable image analysis techniques or machine learning processing functionality configured to determine whether a desired view has been obtained. Additionally and/or alternatively, the artificial intelligence image analysis techniques or machine learning processing functionality configured to provide the image analysis techniques may be provided by a different processor or distributed across multiple processors at the ultrasound system 100 and/or a remote processor communicatively coupled to the ultrasound system 100. In various embodiments, the image analysis processor 140 may comprise suitable logic, circuitry, interfaces and/or code that may be operable to provide a quality metric associated with the obtained view. For example, the image analysis processor 140 may analyze the obtained ultrasound image view as a whole, regions of the obtained ultrasound image view, the obtained ultrasound image view segmented by the segmentation processor 150, or the like to provide a quality metric associated with the obtained view. The image analysis processor 140 may be configured to cause the display system 134 to present the quality metric with the obtained ultrasound image view. For example, the quality metric may be a score (e.g., 1, 2, 3, 4, 5), grade (e.g., A, B, C, D, F), rating (e.g., Excellent, Good, Fair, Poor), color-coding (e.g., green, yellow, red), or the like of the obtained ultrasound image view as a whole and/or for each region of the obtained ultrasound image view. The quality metric may assist a user in determining whether to proceed with the obtained view or to acquire additional ultrasound image data. The image analysis processor 140 may store the quality metric at archive and/or any suitable data storage medium.

The signal processor 132 may include a segmentation processor 150 that comprises suitable logic, circuitry, interfaces and/or code that may be operable to segment flow image frames and B-mode frames. The segmentation processor 150 may be used to identify a liver and a renal cortex of a kidney in the obtained ultrasound image view, such as the Morison's pouch view. In this regard, the segmentation processor 150 may include, for example, artificial intelligence image analysis algorithms, one or more deep neural networks (e.g., a convolutional neural network such as u-net) and/or may utilize any suitable form of artificial intelligence image analysis techniques or machine learning processing functionality configured to provide automated segmentation functionality. Additionally and/or alternatively, the artificial intelligence image analysis techniques or machine learning processing functionality configured to provide the automated segmentation may be provided by a different processor or distributed across multiple processors at the ultrasound system 100 and/or a remote processor communicatively coupled to the ultrasound system 100. For example, the image segmentation functionality may be provided as a deep neural network that may be made up of, for example, an input layer, an output layer, and one or more hidden layers in between the input and output layers. Each of the layers may be made up of a plurality of processing nodes that may be referred to as neurons. For example, the image segmentation functionality may include an input layer having a neuron for each sample or a group of samples from an obtained ultrasound image view of the liver and a kidney. The output layer may have a neuron corresponding to a plurality of pre-defined anatomical structures, such as a liver, a renal cortex, or any suitable anatomical structure. Each neuron of each layer may perform a processing function and pass the processed ultrasound image information to one of a plurality of neurons of a downstream layer for further processing. As an example, neurons of a first layer may learn to recognize edges of structure in the obtained ultrasound image. The neurons of a second layer may learn to recognize shapes based on the detected edges from the first layer. The neurons of a third layer may learn positions of the recognized shapes relative to landmarks in the obtained ultrasound image. The processing performed by the deep neural network may identify anatomical structures and the location of the structures in the obtained ultrasound image with a high degree of probability.

In an exemplary embodiment, the segmentation processor 150 may be configured to store the image segmentation information at archive 138 and/or any suitable storage medium. The segmentation processor 150 may be configured to cause the display system 134 to present the image segmentation information with the obtained ultrasound image. The image segmentation information may be provided to the image analysis processor 140 for providing a quality metric associated with the obtained ultrasound image view as discussed above. The image segmentation information may be provided to the sample identification processor 160 for identifying valid samples in the liver and renal cortex portions of the obtained ultrasound image, as described below.

Figure 2:
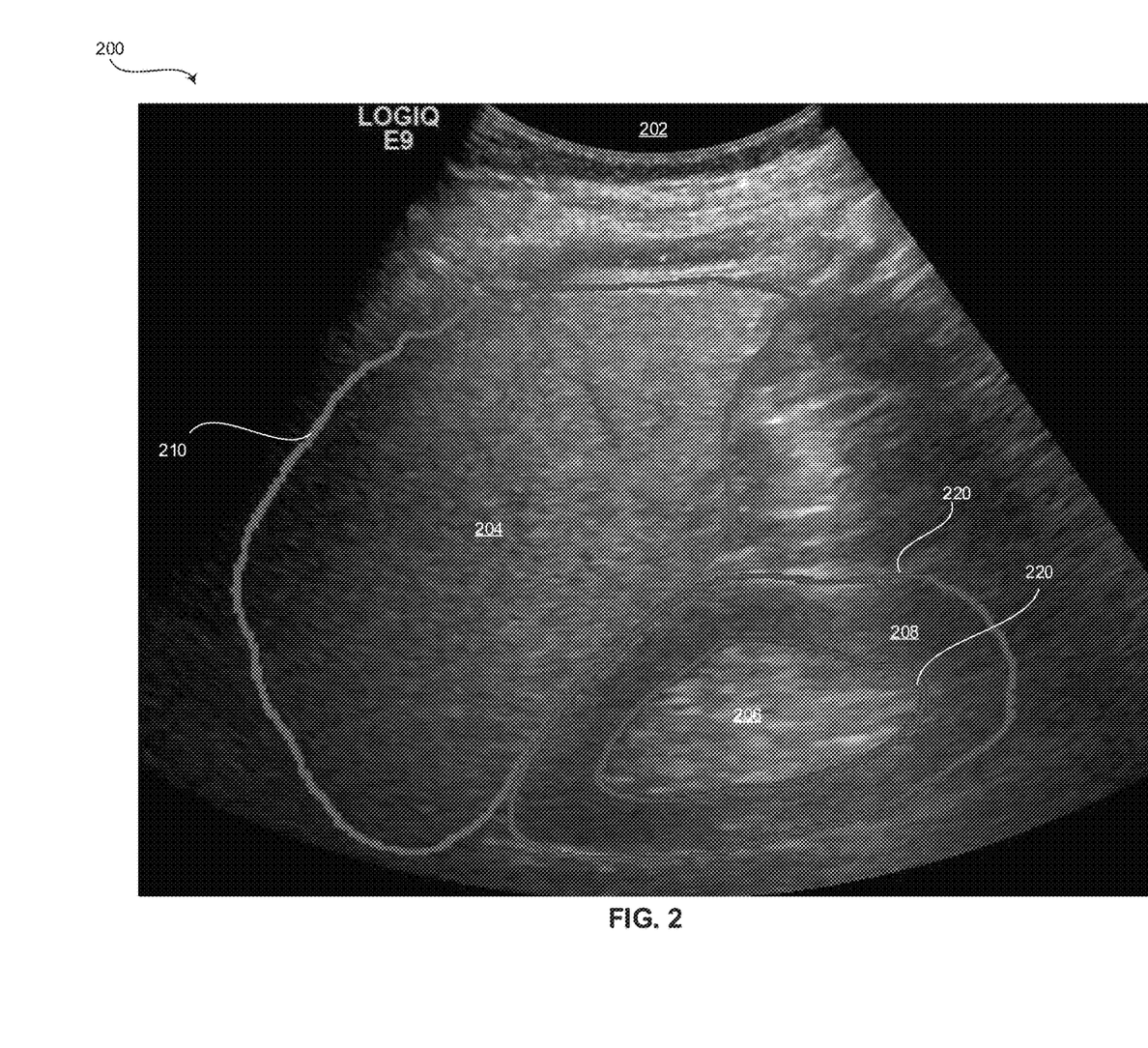
FIG. 2 is an exemplary display of a Morison's pouch ultrasound image view having an anatomical segmentation of a liver and renal cortex, in accordance with various embodiments.

FIG. 2 is an exemplary display 200 of a Morison's pouch ultrasound image view 202 having an anatomical segmentation 210, 220 of a liver 204 and renal cortex 208, in accordance with various embodiments. Referring to FIG. 2, a display 200 includes an obtained ultrasound image view 202, such as a Morison's pouch ultrasound image view 202 having a liver 204 and a kidney 206. The segmentation processor 150 may perform image segmentation 210, 220 on the obtained ultrasound image view 202 to identify a liver 204 and a renal cortex 208 of a kidney 206. The obtained ultrasound image view 202 having the segmented 210 liver 204 and segmented 220 renal cortex 208 of the kidney 206 may be displayed 200 at the display system 134, provided to the image analysis processor 140, provided to the sample identification processor 160, and/or stored at archive 138 and/or any suitable data storage medium.

The signal processor 132 may include a sample identification processor 160 that comprises suitable logic, circuitry, interfaces and/or code that may be operable to identify valid samples in the liver 204 and renal cortex 208 in the obtained ultrasound image view 202 by excluding invalid samples. For example, the sample identification processor 160 may identify valid samples based on exclusion of invalid samples from the liver 204 and renal cortex 208 in the obtained ultrasound image view 202. The sample identification processor 160 may exclude samples from the segmented 210 liver 204 of the obtained ultrasound image view 202 by applying artificial intelligence algorithms and/or any suitable image analysis technique to exclude samples inside large ducts, vessels, masses, and cysts in the liver 204. The sample identification processor 160 may apply artificial intelligence algorithms and/or any suitable image analysis technique to exclude samples in the segmented 210 liver 204 having artifacts and/or in artifact prone regions. The sample identification processor 160 may apply artificial intelligence algorithms and/or any suitable image analysis technique to exclude samples in the segmented 210 liver 204 within a threshold distance from a boundary of the liver 204. The sample identification processor 160 may apply artificial intelligence algorithms and/or any suitable image analysis technique to identify valid samples in the segmented 210 liver 204 in only homogenous regions of the segmented 210 liver 204. The sample identification processor 160 may apply artificial intelligence algorithms and/or any suitable image analysis technique to exclude samples in the segmented 210 liver 204 having sample values above an upper threshold or below a lower threshold. The sample identification processor 160 may apply artificial intelligence algorithms and/or any suitable image analysis technique to exclude samples in the segmented 210 liver 204 that are greater than a threshold distance from the kidney 206.

The sample identification processor 160 may apply artificial intelligence algorithms and/or any suitable image analysis technique to exclude samples inside masses, cysts, collecting system, and external renal tissue in the segmented 210 renal cortex 208. The sample identification processor 160 may apply artificial intelligence algorithms and/or any suitable image analysis technique to exclude samples in the segmented 210 renal cortex 208 having artifacts and/or in artifact prone regions. The sample identification processor 160 may apply artificial intelligence algorithms and/or any suitable image analysis technique to exclude samples in the segmented 210 renal cortex 208 within a threshold distance from a boundary of the kidney 206. The sample identification processor 160 may apply artificial intelligence algorithms and/or any suitable image analysis technique to identify valid samples in the segmented 210 renal cortex 208 in only homogenous regions of the segmented 210 renal cortex 208. The sample identification processor 160 may apply artificial intelligence algorithms and/or any suitable image analysis technique to exclude samples in the segmented 210 renal cortex 208 having sample values above an upper threshold or below a lower threshold. The sample identification processor 160 may apply artificial intelligence algorithms and/or any suitable image analysis technique to exclude samples in the segmented 210 renal cortex 208 that are greater than a threshold distance from the liver 204.

In various embodiments, the sample identification processor 160 may be configured to identify the valid samples with highlighting, shading, labeling, and/or any suitable visual indication. The obtained ultrasound image view 202 having the visual indication of the identified samples may be displayed at the display system 134. Additionally and/or alternatively, the sample identification processor 160 may provide the obtained ultrasound image view 202 having the identified valid samples (with or without a visual indication) to the ROI positioning processor 170. The sample identification processor 160 may additionally and/or alternatively store the obtained ultrasound image view 202 having the identified valid samples (with or without a visual indication) to archive 138 and/or any suitable data storage medium.

Figure 3:
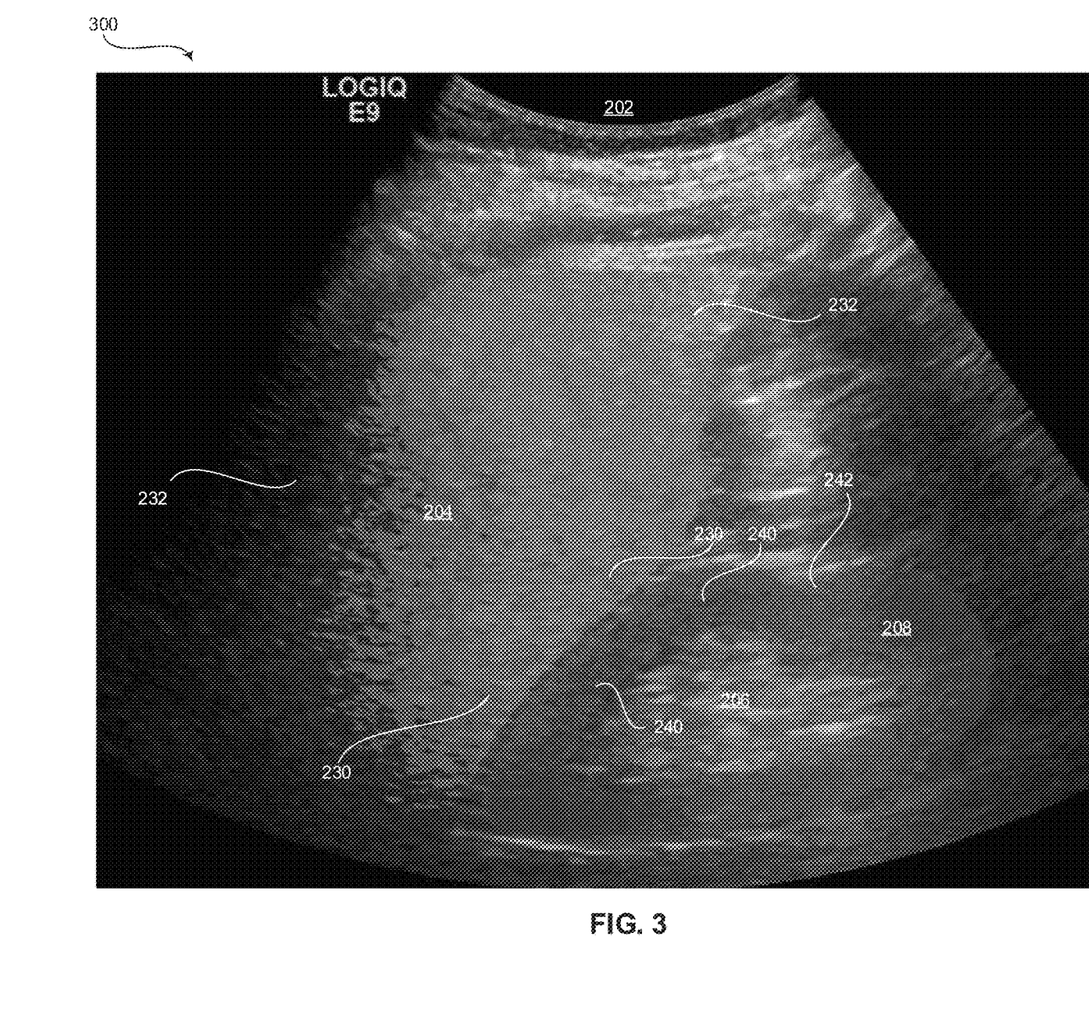
FIG. 3 is an exemplary display of the segmented Morison's pouch ultrasound image view of FIG. 2 having identified valid samples, in accordance with various embodiments.

FIG. 3 is an exemplary display 300 of the segmented Morison's pouch ultrasound image view 202 of FIG. 2 having identified valid samples 230, 240, in accordance with various embodiments. Referring to FIG. 3, a display 300 includes the segmented ultrasound image view 202 of FIG. 2 depicting a Morison's pouch ultrasound image view 202 having a liver 204 and a kidney 206. The sample identification processor 160 may apply sample identification algorithms on the segmented ultrasound image view 202 to identify valid samples of the liver 204 and the renal cortex 208 of the kidney 206. The sample identification processor 160 may be configured to identify the valid samples with highlighting, shading, labeling, and/or any suitable visual indication 230, 240. The segmented ultrasound image view 202 having the visual indication 230 of the identified valid samples of the liver 204 and the visual indication 240 of the identified valid samples of the renal cortex 208 may be displayed 300 at the display system 134. The samples 232, 242 of the segmented liver 204 and renal cortex 208 excluded by the sample identification processor 160 may not include a visual indication or may be provided with a different visual indication from the valid samples 230, 240. The segmented ultrasound image view 202 having the identified valid samples 230 of the liver 204 and the identified valid samples 240 of the renal cortex 208 of the kidney 206 may be displayed 300 at the display system 134, provided to the ROI positioning processor 170, and/or stored at archive 138 and/or any suitable data storage medium.

The signal processor 132 may include a region of interest (ROI) positioning processor 170 that comprises suitable logic, circuitry, interfaces and/or code that may be operable to automatically position a liver region of interest and a renal cortex region of interest in the obtained ultrasound image view 202 based on the identified valid samples 230, 240 and at least one criterion. For example, the ROI positioning processor 170 may be configured to apply algorithms defined by the at least one criterion to the valid samples 230, 240 of the obtained ultrasound image view 202 to identify a densest valid sample region in the renal cortex 208 of the kidney 206 and the densest valid sample region in the liver 204. The ROI positioning processor 170 may determine the densest valid sample region of the liver 204 based at least in part on one or more of a shortest distance to a center line of the transducer data, a shortest distance to the densest valid sample region of the renal cortex 208, the densest valid sample region of the liver 204 at a same image depth as the densest valid sample region of the renal cortex 208, and/or the densest valid sample region of the liver 204 at a same geometrical depth (e.g., if using a curved array transducer) as the densest valid sample region of the renal cortex 208. The ROI positioning processor 170 may be configured to provide visual indications of the liver region of interest and the renal cortex region of interest in the obtained ultrasound image view 202. The visual indications of the regions of interest may include highlighting, shading, labeling, overlaid shapes, and/or any suitable visual indications. The obtained ultrasound image view 202 having the visual indications of the liver region of interest and the renal cortex region of interest may be displayed at the display system 134. Additionally and/or alternatively, the ROI positioning processor 170 may provide the obtained ultrasound image view 202 having the positioned liver region of interest and renal cortex region of interest (with or without visual indications) to the HRI processor 180. The ROI positioning processor 170 may additionally and/or alternatively store the obtained ultrasound image view 202 having the positioned liver region of interest and renal cortex region of interest (with or without visual indications) to archive 138 and/or any suitable data storage medium.

Figure 4:
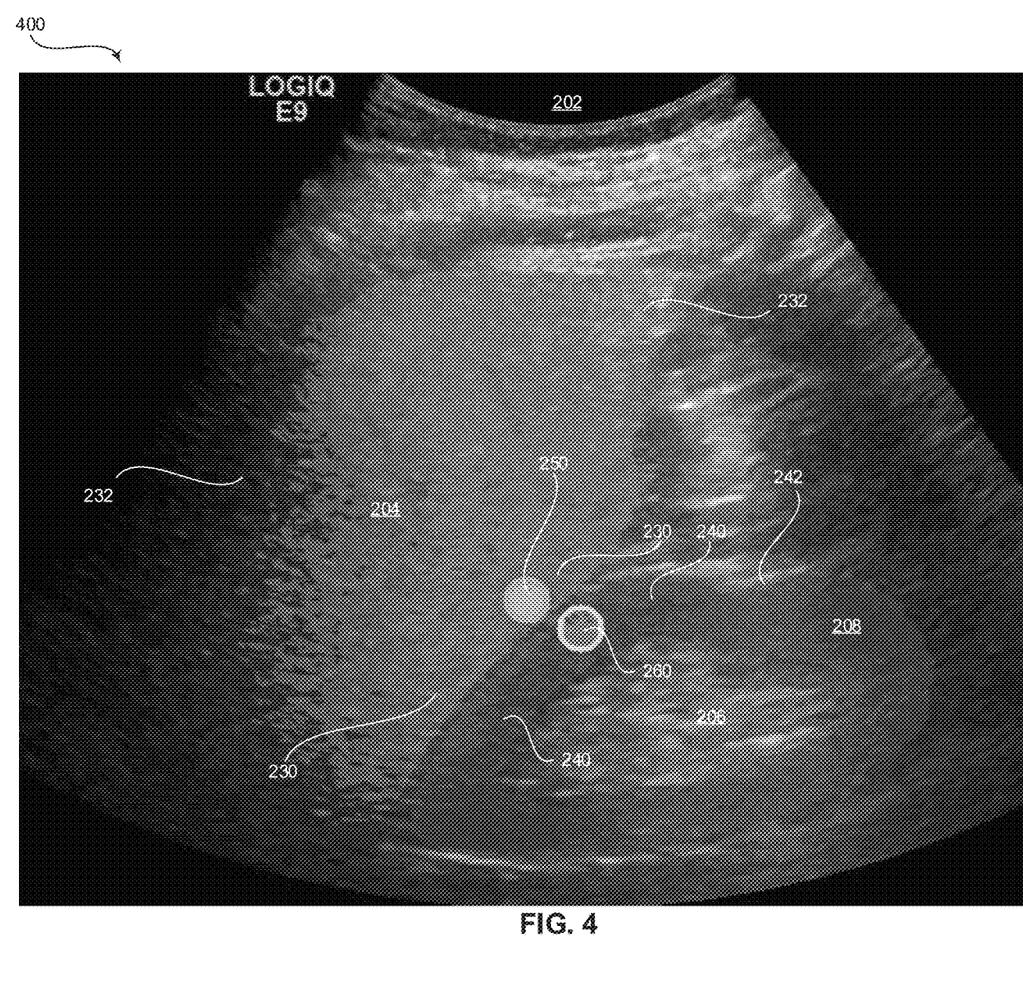
FIG. 4 is an exemplary display of the segmented Morison's pouch ultrasound image view having identified valid samples of FIG. 3 with automatically positioned liver and renal cortex regions of interest for HRI calculation, in accordance with various embodiments.

FIG. 4 is an exemplary display 400 of the segmented Morison's pouch ultrasound image view 202 having identified valid samples 230, 240 of FIG. 3 with automatically positioned liver and renal cortex regions of interest 250, 260 for HRI calculation, in accordance with various embodiments. Referring to FIG. 4, a display 400 includes the segmented ultrasound image view 202 of FIG. 3 depicting a Morison's pouch ultrasound image view 202 having a liver 204 and a kidney 206 with identified valid samples 230, 240. The ROI positioning processor 170 may automatically position a liver region of interest 250 and a renal cortex region of interest 260 in the obtained ultrasound image view 202 based on the identified valid samples 230, 240 and at least one criterion. The ROI positioning processor 170 may be configured to identify the liver and renal cortex regions of interest 250, 260 with highlighting, shading, labeling, overlaid shapes, and/or any suitable visual indication. The segmented ultrasound image view 202 having the automatically positioned liver and renal cortex regions of interest 250, 260 may be displayed 400 at the display system 134, provided to the HRI processor 180, and/or stored at archive 138 and/or any suitable data storage medium. In various embodiments, a clinician may re-position the automatically positioned liver and/or renal cortex regions of interest 250, 260 via the user input device 130.

The signal processor 132 may include a hepatorenal index (HRI) processor 180 that comprises suitable logic, circuitry, interfaces and/or code that may be operable to determine an HRI based on the liver and renal cortex regions of interest 250, 260 in the segmented ultrasound image view 202. For example, the HRI processor 180 may determine the HRI by calculating a ratio of the liver data in the liver region of interest 250 to the renal cortex data in the renal cortex region of interest 260. The liver data and renal cortex data may comprise the beamformed data, in-phase and quadrature (I/Q) data, post-processed data, or grayscale values. The HRI processor 180 may be configured to cause the display system 134 to present the HRI value. In certain embodiments, the HRI processor 180 may be configured to determine a quality score corresponding with the determined HRI value. For example, the HRI processor 180 may apply a quality score algorithm based on a standard deviation from multiple regions of interest in the liver 204 and renal cortex 208 of the segmented ultrasound image view 202. The HRI processor 180 may be configured to cause the display system 134 to present the quality score with the HRI value.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as ultrasound images 202 with and/or without image quality metrics, segmentation information 210, 220, valid 230, 240 and/or invalid 232, 242 sample information, regions of interest 250, 260, HRI values, HRI quality scores, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), an enterprise archive (EA), a vendor-neutral archive (VNA), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound images 202, image quality metrics generated by the image analysis processor 140, instructions for analyzing the ultrasound images 202 and generating the image quality metrics, segmentation information generated by the segmentation processor 150, instructions for performing image segmentation, valid and/or invalid sample information 230, 232, 240, 242 generated by the sample identification processor 160, instructions for identifying valid samples 230, 240, region of interest information 250, 260 generated by the ROI positioning processor 170, instructions for automatically positioning regions of interest 250, 260, HRI values generated by the HRI processor 180, instructions for determining HRI values, HRI quality scores generated by the HRI processor 180, and/or instructions for generating HRI quality scores, among other things.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 160 may comprise suitable logic, circuitry, interfaces and/or code that may be operable to train the neurons of the deep neural network(s) (e.g., artificial intelligence model(s)) inferenced (i.e., deployed) by the image analysis processor 140, segmentation processor 150, sample identification processor 160, ROI positioning processor 170, and/or HRI processor 180. For example, the artificial intelligence model inferenced by the image analysis processor 140 may be trained to automatically identify an ultrasound image view (e.g., a Morison's pouch ultrasound image view 202). The artificial intelligence model inferenced by the segmentation processor 150 may be trained to automatically segment an obtained ultrasound image view to identify anatomies (e.g., a liver 204 and a renal cortex 208 of a kidney 206). As an example, the training engine 210 may train the deep neural networks deployed by the image analysis processor 140 and/or segmentation processor 150 using database(s) 220 of classified Morison's pouch ultrasound image views of a liver 204 and a renal cortex 208 of a kidney 206. The ultrasound images may include ultrasound images of a particular anatomical feature, such as Morison's pouch ultrasound image views 202 having a liver 204 and a renal cortex 208 of a kidney 206, or any suitable ultrasound images and features.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 5:
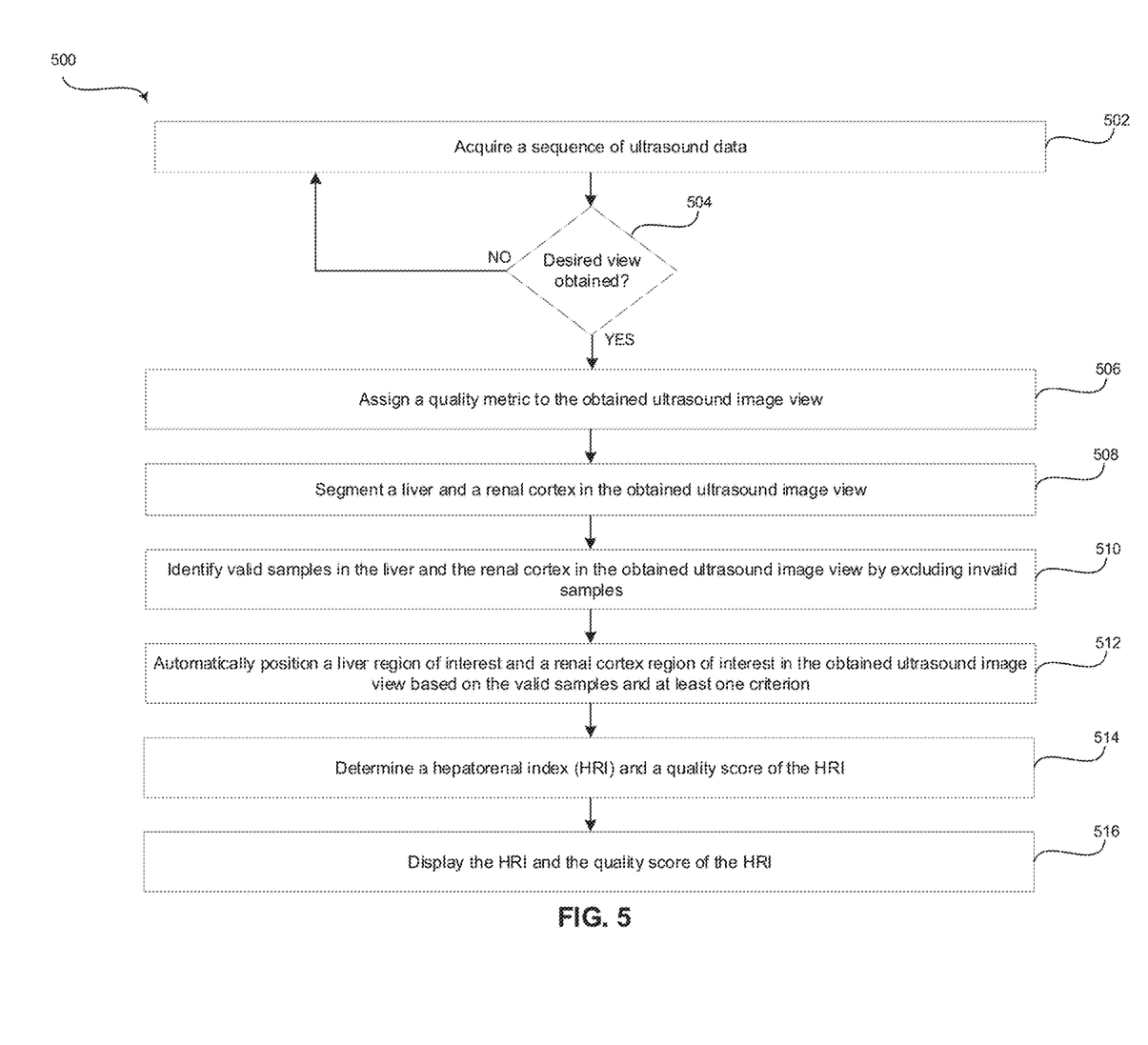
FIG. 5 is a flow chart illustrating exemplary steps that may be utilized for automatically estimating an HRI from ultrasound images, in accordance with exemplary embodiments.

FIG. 5 is a flow chart 500 illustrating exemplary steps 502-516 that may be utilized for automatically estimating an HRI from ultrasound images, in accordance with exemplary embodiments. Referring to FIG. 5, there is shown a flow chart 500 comprising exemplary steps 502 through 516. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 502, an ultrasound system 100 may acquire a sequence of ultrasound data. For example, the ultrasound probe 104 of the ultrasound system 100 may continuously acquire ultrasound image data until a desired ultrasound image view is obtained. The acquired sequence of ultrasound data may be processed and presented at a display system 134.

At step 504, a signal processor 132 of the ultrasound system 100 may determine whether a desired ultrasound image view 202 has been obtained. For example, an image analysis processor 140 of the signal processor 132 of the ultrasound system 100 may analyze the ultrasound image data acquired at step 502 to determine whether a desired ultrasound image view 202 has been obtained. The desired ultrasound image view 202 may be a Morison's pouch ultrasound image view or any suitable ultrasound image view of the liver 204 and kidney 206. The image analysis processor 140 may direct the signal processor 132 to freeze the view presented at the display system 134 once the desired image view is obtained. The image analysis processor 140 may include, for example, artificial intelligence image analysis algorithms, one or more deep neural networks (e.g., a convolutional neural network such as u-net) and/or may utilize any suitable image analysis techniques or machine learning processing functionality configured to determine whether a desired view has been obtained.

At step 506, the signal processor 132 of the ultrasound system 100 may assign a quality metric to the obtained ultrasound image view 202. For example, the image analysis processor 140 may analyze the obtained ultrasound image view 202 as a whole, regions of the obtained ultrasound image view 202, the obtained ultrasound image view segmented by the segmentation processor 150 at step 508, or the like to provide a quality metric associated with the obtained ultrasound image view 202. The image analysis processor 140 may be configured to cause the display system 134 to present the quality metric with the obtained ultrasound image view 202.

At step 508, a signal processor 132 of the ultrasound system 100 may segment 210, 220 a liver 204 and a renal cortex 208 in the obtained ultrasound image view 202. For example, a segmentation processor 140 of the signal processor 132 may be configured to identify 210, 220 a liver 204 and a renal cortex 208 of a kidney 206 in the obtained ultrasound image view 202, such as the Morison's pouch view. The segmentation processor 150 may include, for example, artificial intelligence image analysis algorithms, one or more deep neural networks (e.g., a convolutional neural network such as u-net) and/or may utilize any suitable form of artificial intelligence image analysis techniques or machine learning processing functionality configured to provide automated segmentation functionality. The segmentation processor 150 may be configured to cause the display system 134 to present the image segmentation information 210, 220 with the obtained ultrasound image 202.

At step 510, the signal processor 132 of the ultrasound system 100 may identify valid samples 230, 240 in the liver 204, 210 and the renal cortex 208, 220 in the obtained ultrasound image view 202 by excluding invalid samples 232, 242. For example, a sample identification processor 160 of the signal processor 132 of the ultrasound system 100 may be configured to exclude samples 232 from the segmented 210 liver 204 of the obtained ultrasound image view 202 by applying artificial intelligence algorithms and/or any suitable image analysis technique to exclude samples 232 inside large ducts, vessels, masses, and cysts in the liver 204, samples 232 in the segmented 210 liver 204 having artifacts and/or in artifact prone regions, samples 232 in the segmented 210 liver 204 within a threshold distance from a boundary of the liver 204, samples 232 in the segmented 210 liver 204 in non-homogenous regions, samples in the segmented 210 liver 204 having sample values above an upper threshold or below a lower threshold, and/or samples in the segmented 210 liver 204 that are greater than a threshold distance from the kidney 206. As another example, the sample identification processor 160 may apply artificial intelligence algorithms and/or any suitable image analysis technique to exclude samples 242 inside masses, cysts, collecting system, and external renal tissue in the segmented 210 renal cortex 208, samples 242 in the segmented 210 renal cortex 208 having artifacts and/or in artifact prone regions, samples 242 in the segmented 210 renal cortex 208 within a threshold distance from a boundary of the kidney 206, samples 242 in the segmented 210 renal cortex 208 in non-homogenous regions, samples 242 in the segmented 210 renal cortex 208 having sample values above an upper threshold or below a lower threshold, and/or samples 242 in the segmented 210 renal cortex 208 that are greater than a threshold distance from the liver 204. The sample identification processor 160 may be configured to identify the valid samples with highlighting, shading, labeling, and/or any suitable visual indication. The obtained ultrasound image view 202 having the visual indication of the identified samples may be displayed at the display system 134.

At step 512, the signal processor 132 of the ultrasound system 100 may automatically position a liver region of interest 250 and a renal cortex region of interest 260 in the obtained ultrasound image view 202 based on the valid samples 230, 240 and at least one criterion. For example, a region of interest (ROI) positioning processor 170 of the signal processor 132 of the ultrasound system 100 may be configured to apply algorithms defined by the at least one criterion to the valid samples 230, 240 of the obtained ultrasound image view 202 to identify a densest valid sample region in the renal cortex 208 of the kidney 206 and the densest valid sample region in the liver 204. The ROI positioning processor 170 may determine the densest valid sample region of the liver 204 based at least in part on one or more of a shortest distance to a center line of the transducer data, a shortest distance to the densest valid sample region of the renal cortex 208, the densest valid sample region of the liver 204 at a same image depth as the densest valid sample region of the renal cortex 208, and/or the densest valid sample region of the liver 204 at a same geometrical depth (e.g., if using a curved array transducer) as the densest valid sample region of the renal cortex 208. The ROI positioning processor 170 may be configured to provide visual indications of the liver region of interest 250 and the renal cortex region of interest 260 in the obtained ultrasound image view 202. The visual indications of the regions of interest may include highlighting, shading, labeling, overlaid shapes, and/or any suitable visual indications. The obtained ultrasound image view 202 having the visual indications of the liver region of interest and the renal cortex region of interest may be displayed at the display system 134. In various embodiments, a clinician may re-position the automatically positioned liver and/or renal cortex regions of interest 250, 260 via the user input device 130.

At step 514, the signal processor 132 of the ultrasound system 100 may determine a hepatorenal index (HRI) and a quality score of the HRI. For example, an HRI processor 180 of the signal processor 132 of the ultrasound system 100 may be configured to determine an HRI based on the liver and renal cortex regions of interest 250, 260 in the segmented ultrasound image view 202. The HRI processor 180 may determine the HRI by calculating a ratio of the liver data in the liver region of interest 250 to the renal cortex data in the renal cortex region of interest 260. The liver data and renal cortex data may comprise beamformed data, in-phase and quadrature (I/Q) data, post-processed data, or grayscale values. In certain embodiments, the HRI processor 180 may be configured to determine a quality score corresponding with the determined HRI value. As an example, the HRI processor 180 may apply a quality score algorithm based on a standard deviation from multiple regions of interest in the liver 204 and renal cortex 208 of the segmented ultrasound image view 202.

At step 516, the signal processor 132 of the ultrasound system 100 may display the HRI and the quality score of the HRI. For example, the HRI processor 180 may be configured to cause the display system 134 to present the HRI value and the quality score of the HRI.

Aspects of the present disclosure provide automatic estimates of a hepatorenal index (HRI) from ultrasound images 202. In accordance with various embodiments, the method 500 may comprise acquiring 502, by an ultrasound system 100, a sequence of ultrasound image data until a desired ultrasound image view 202 is obtained 504. The method 500 may comprise segmenting 508, by at least one processor 132, 150 of the ultrasound system 100, a liver 204, 210 and a renal cortex 208, 220 in the obtained ultrasound image view 202. The method 500 may comprise identifying 510, by the at least one processor 132, 160, valid samples 230, 240 in the liver 204, 210 and the renal cortex 208, 220 in the obtained ultrasound image view 202 by excluding invalid samples 232, 242. The method 500 may comprise automatically positioning 512, by the at least one processor 132, 170, a liver region of interest 250 and a renal cortex region of interest 260 in the obtained ultrasound image view 202 based on the valid samples 230, 240 and at least one criterion. The method 500 may comprise determining 514, by the at least one processor 132, 180, a hepatorenal index (HRI). The method 500 may comprise causing 516, by the at least one processor 132, 180, a display system 134 to present the HRI.

In a representative embodiment, the method 500 may comprise determining 514, by the at least one processor 132, 180, a quality score of the HRI and causing, by the at least one processor 132, 180, the display system 134 to present the quality score of the HRI with the HRI. In an exemplary embodiment, the method 500 may comprise assigning 506, by the at least one processor 132, 140, a quality metric to the obtained ultrasound image view 202 and causing 506, by the at least one processor 132, 140, the display system 134 to present the quality metric. In various embodiments, the invalid samples 232 in the liver 204, 210 comprise one or more of: samples inside one or more of ducts, vessels, masses, and cysts; one or both of samples depicting artifacts or samples in artifact prone regions; samples within a threshold distance to a liver boundary line; samples in non-homogenous regions inside the liver 204, 210; samples having values above an upper threshold or below a lower threshold; and samples greater than a defined distance from the kidney 206, 208. In certain embodiments, the invalid samples 242 in the renal cortex 208, 220 comprise one or more of: samples inside one or more of masses, cysts, collecting system, and external renal tissue; one or both of samples depicting artifacts or samples in artifact prone regions; samples within a threshold distance to a kidney boundary line; samples in non-homogenous regions inside the renal cortex 208, 220; and samples having values above an upper threshold or below a lower threshold. In a representative embodiment, the at least one criterion comprises one or both of a densest valid sample region in the renal cortex 208, 220 and a densest valid sample region in the liver 204, 210. The densest valid sample region in the liver 204, 210 may be identified based at least in part on one or more of: a shortest distance to a center line of transducer data; a shortest distance to the densest valid sample region in the renal cortex 208, 220; the densest valid sample region in the liver 204, 210 being at a same image depth as the densest valid sample region in the renal cortex 208, 220; and the densest valid sample region in the liver 204, 210 being at a same geometrical depth as the densest valid sample region in the renal cortex 208, 220. In an exemplary embodiment, determining the HRI is based on a ratio of an average of liver data in the liver region of interest 250 and an average of renal cortex data in the renal cortex region of interest 260. The liver data and the renal cortex data may be one of beamformed data, in-phase and quadrature (I/Q) data, post-processed data, and grayscale values.

Various embodiments provide an ultrasound system 100 for automatically estimating a hepatorenal index (HRI) from ultrasound images. The ultrasound system 100 may comprise an ultrasound probe 104, at least one processor 132, 140, 150, 160, 170, 180 and a display system 134. The ultrasound probe 104 may be operable to acquire a sequence of ultrasound image data until a desired ultrasound image view 202 is obtained. The at least one processor 132, 150 may be configured to segment a liver 204, 210 and a renal cortex 208, 220 in the obtained ultrasound image view 202. The at least one processor 132, 160 may be configured to identify valid samples 230, 240 in the liver 204, 210 and the renal cortex 208, 220 in the obtained ultrasound image view 202 by excluding invalid samples 232, 242. The at least one processor 132, 170 may be configured to automatically position a liver region of interest 250 and a renal cortex region of interest 260 in the obtained ultrasound image view 202 based on the valid samples 230, 240 and at least one criterion. The at least one processor 132, 180 may be configured to determine a hepatorenal index (HRI). The display system 134 may be configured to present the HRI.

In an exemplary embodiment, the at least one processor 132, 180 may be configured to determine a quality score of the HRI and cause the display system 134 to present the quality score of the HRI with the HRI. In various embodiments, the at least one processor 132, 140 may be configured to assign a quality metric to the obtained ultrasound image view 202 and cause the display system 134 to present the quality metric. In certain embodiments, the invalid samples 232 in the liver 204, 210 comprise one or more of: samples inside one or more of ducts, vessels, masses, and cysts; one or both of samples depicting artifacts or samples in artifact prone regions; samples within a threshold distance to a liver boundary line; samples in non-homogenous regions inside the liver 204, 210; samples having values above an upper threshold or below a lower threshold; and samples greater than a defined distance from the kidney 206, 208. In a representative embodiment, the invalid samples 242 in the renal cortex 208, 220 comprise one or more of: samples inside one or more of masses, cysts, collecting system, and external renal tissue; one or both of samples depicting artifacts or samples in artifact prone regions; samples within a threshold distance to a kidney boundary line; samples in non-homogenous regions inside the renal cortex; and samples having values above an upper threshold or below a lower threshold. In an exemplary embodiment, the at least one criterion may comprise one or both of a densest valid sample region in the renal cortex 208, 220 and a densest valid sample region in the liver 204, 210. The densest valid sample region in the liver 204, 210 may be identified based at least in part on one or more of: a shortest distance to a center line of transducer data; a shortest distance to the densest valid sample region in the renal cortex 208, 220; the densest valid sample region in the liver 204, 210 being at a same image depth as the densest valid sample region in the renal cortex 208, 220; and the densest valid sample region in the liver 204, 210 being at a same geometrical depth as the densest valid sample region in the renal cortex 208, 220. In various embodiments, the at least one processor 132, 180 configured to determine the HRI based on a ratio of an average of liver data in the liver region of interest 250 and an average of renal cortex data in the renal cortex region of interest 260. The liver data and the renal cortex data may be one of beamformed data, in-phase and quadrature (I/Q) data, post-processed data, and grayscale values.

Certain embodiments provide a non-transitory computer readable medium having stored thereon, a computer program having at least one code section. The at least one code section is executable by a machine for causing an ultrasound system to perform steps 500. The steps 500 may comprise receiving 502 a sequence of ultrasound image data until a desired ultrasound image view 202 is received 504. The steps 500 may comprise segmenting 508 a liver 204, 210 and a renal cortex 208, 220 in the received ultrasound image view 202. The steps 500 may comprise identifying 510 valid samples 230, 240 in the liver 204, 210 and the renal cortex 208, 220 in the received ultrasound image view 202 by excluding invalid samples 232, 242. The steps 500 may comprise automatically positioning 512 a liver region of interest 250 and a renal cortex region of interest 260 in the received ultrasound image view 202 based on the valid samples 230, 240 and at least one criterion. The steps 500 may comprise determining 514 a hepatorenal index (HRI). The steps 500 may comprise causing 516 a display system 134 to present the HRI.

In various embodiments, the steps 500 may comprise assigning 506 a quality metric to the received ultrasound image view 202 and causing the display system 134 to present the quality metric. The steps 500 may comprise determining 514 a quality score of the HRI and causing 516 the display system 134 to present the quality score of the HRI with the HRI. In certain embodiments, the invalid samples 232 in the liver 204, 210 may comprise one or more of: samples inside one or more of ducts, vessels, masses, and cysts; one or both of samples depicting artifacts or samples in artifact prone regions; samples within a threshold distance to a liver boundary line; samples in non-homogenous regions inside the liver 204, 210; samples having values above an upper threshold or below a lower threshold; and samples greater than a defined distance from the kidney 206, 208. In a representative embodiment, the invalid samples 242 in the renal cortex 208, 220 may comprise one or more of: samples inside one or more of: masses, cysts, collecting system, and external renal tissue; one or both of samples depicting artifacts or samples in artifact prone regions; samples within a threshold distance to a kidney boundary line; samples in non-homogenous regions inside the renal cortex 208, 220; and samples having values above an upper threshold or below a lower threshold.

In an exemplary embodiment, the at least one criterion may comprise one or both of a densest valid sample region in the renal cortex 208, 220 and a densest valid sample region in the liver 204, 210. The densest valid sample region in the liver 204, 210 may be identified based at least in part on one or more of: a shortest distance to a center line of transducer data; a shortest distance to the densest valid sample region in the renal cortex 208, 220; the densest valid sample region in the liver 204, 210 being at a same image depth as the densest valid sample region in the renal cortex 208, 220; and the densest valid sample region in the liver 204, 210 being at a same geometrical depth as the densest valid sample region in the renal cortex 208, 220. In various embodiments, determining 514 the HRI may be based on a ratio of an average of liver data in the liver region of interest 250 and an average of renal cortex data in the renal cortex region of interest 260. The liver data and the renal cortex data may be one of beamformed data, in-phase and quadrature (I/Q) data, post-processed data, and grayscale values.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically estimating a hepatorenal index (HRI) from ultrasound images.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   acquiring, by an ultrasound system, a sequence of ultrasound image data until a desired ultrasound image view is obtained;
   segmenting, by at least one processor of the ultrasound system, a liver and a renal cortex in the obtained ultrasound image view;
   identifying, by the at least one processor, valid samples in the liver and the renal cortex in the obtained ultrasound image view by excluding invalid samples;
   automatically positioning, by the at least one processor, a liver region of interest and a renal cortex region of interest in the obtained ultrasound image view by applying at least one criterion to the valid samples after the excluding the invalid samples;
   determining, by the at least one processor, a hepatorenal index (HRI);
   determining, by the at least one processor, a quality score of the HRI based on a standard deviation from a plurality of the liver region of interest and a plurality of the renal cortex region of interest; and
   causing, by the at least one processor, a display system to present the quality score of the HRI with the HRI.

2. The method of claim 1, comprising:
   assigning, by the at least one processor, a quality metric to the obtained ultrasound image view; and
   causing, by the at least one processor, the display system to present the quality metric.

3. The method of claim 1, wherein the invalid samples in the liver comprise one or more of:
   samples inside one or more of ducts, vessels, masses, and cysts;
   one or both of samples depicting artifacts or samples in artifact prone regions;
   samples within a threshold distance to a liver boundary line;
   samples in non-homogenous regions inside the liver;
   samples having values above an upper threshold or below a lower threshold; and
   samples greater than a defined distance from the kidney.

4. The method of claim 1, wherein the invalid samples in the renal cortex comprise one or more of:
   samples inside one or more of masses, cysts, collecting system, and external renal tissue;
   one or both of samples depicting artifacts or samples in artifact prone regions;
   samples within a threshold distance to a kidney boundary line;
   samples in non-homogenous regions inside the renal cortex; and
   samples having values above an upper threshold or below a lower threshold.

5. The method of claim 1, wherein the at least one criterion comprises one or both of:
   a densest valid sample region in the renal cortex; and
   a densest valid sample region in the liver, wherein the densest valid sample region in the liver is identified based at least in part on one or more of:
      a shortest distance to a center line of transducer data;
      a shortest distance to the densest valid sample region in the renal cortex;
      the densest valid sample region in the liver being at a same image depth as the densest valid sample region in the renal cortex; and
      the densest valid sample region in the liver being at a same geometrical depth as the densest valid sample region in the renal cortex.

6. The method of claim 1, wherein:
   determining the HRI is based on a ratio of an average of liver data in the liver region of interest and an average of renal cortex data in the renal cortex region of interest, and
   the liver data and the renal cortex data is one of:
      beamformed data,
      in-phase and quadrature (I/Q) data,
      post-processed data, and
      grayscale values.

7. An ultrasound system comprising:
   an ultrasound probe operable to acquire a sequence of ultrasound image data until a desired ultrasound image view is obtained;
   at least one processor configured to:
      segment a liver and a renal cortex in the obtained ultrasound image view;
      identify valid samples in the liver and the renal cortex in the obtained ultrasound image view by excluding invalid samples;
      automatically position a liver region of interest and a renal cortex region of interest in the obtained ultrasound image view by applying at least one criterion to the valid samples after the excluding the invalid samples; and
      determine a hepatorenal index (HRI);
      determine a quality score of the HRI based on a standard deviation from a plurality of the liver region of interest and a plurality of the renal cortex region of interest; and
   a display system configured to present the HRI with the quality score of the HRI.

8. The system of claim 7, wherein the at least one processor is configured to:
   assign a quality metric to the obtained ultrasound image view; and
   cause the display system to present the quality metric.

9. The system of claim 7, wherein the invalid samples in the liver comprise one or more of:
   samples inside one or more of ducts, vessels, masses, and cysts;
   one or both of samples depicting artifacts or samples in artifact prone regions;
   samples within a threshold distance to a liver boundary line;
   samples in non-homogenous regions inside the liver;
   samples having values above an upper threshold or below a lower threshold; and
   samples greater than a defined distance from the kidney.

10. The system of claim 7, wherein the invalid samples in the renal cortex comprise one or more of:
    samples inside one or more of masses, cysts, collecting system, and external renal tissue;
    one or both of samples depicting artifacts or samples in artifact prone regions;
    samples within a threshold distance to a kidney boundary line;
    samples in non-homogenous regions inside the renal cortex; and
    samples having values above an upper threshold or below a lower threshold.

11. The system of claim 7, wherein the at least one criterion comprises one or both of:
    a densest valid sample region in the renal cortex; and
    a densest valid sample region in the liver, wherein the densest valid sample region in the liver is identified based at least in part on one or more of:
       a shortest distance to a center line of transducer data;
       a shortest distance to the densest valid sample region in the renal cortex;
       the densest valid sample region in the liver being at a same image depth as the densest valid sample region in the renal cortex; and
       the densest valid sample region in the liver being at a same geometrical depth as the densest valid sample region in the renal cortex.

12. The system of claim 7, wherein:
    the at least one processor is configured to determine the HRI based on a ratio of an average of liver data in the liver region of interest and an average of renal cortex data in the renal cortex region of interest, and
    the liver data and the renal cortex data is one of:
       beamformed data,
       in-phase and quadrature (I/Q) data,
       post-processed data, and
       grayscale values.

13. A non-transitory computer readable medium having stored thereon, a computer program having at least one code section, the at least one code section being executable by a machine for causing an ultrasound system to perform steps comprising:
    receiving a sequence of ultrasound image data until a desired ultrasound image view is received;
    segmenting a liver and a renal cortex in the received ultrasound image view;
    identifying valid samples in the liver and the renal cortex in the received ultrasound image view by excluding invalid samples;
    automatically positioning a liver region of interest and a renal cortex region of interest in the received ultrasound image view by applying at least one criterion to the valid samples after the excluding the invalid samples;

determining a hepatorenal index (HRI);

determining a quality score of the HRI based on a standard deviation from a plurality of the liver region of interest and a plurality of the renal cortex region of interest; and causing a display system to present the quality score of the HRI with the HRI.

14. The non-transitory computer readable medium of claim 13, comprising the step of:

assigning a quality metric to the received ultrasound image view and causing the display system to present the quality metric.

15. The non-transitory computer readable medium of claim 13, wherein the invalid samples in the liver comprise one or more of:

samples inside one or more of ducts, vessels, masses, and cysts;

one or both of samples depicting artifacts or samples in artifact prone regions;

samples within a threshold distance to a liver boundary line;

samples in non-homogenous regions inside the liver;

samples having values above an upper threshold or below a lower threshold; and samples greater than a defined distance from the kidney.

16. The non-transitory computer readable medium of claim 13, wherein the invalid samples in the renal cortex comprise one or more of:

samples inside one or more of masses, cysts, collecting system, and external renal tissue;

one or both of samples depicting artifacts or samples in artifact prone regions;

samples within a threshold distance to a kidney boundary line;

samples in non-homogenous regions inside the renal cortex; and samples having values above an upper threshold or below a lower threshold.

17. The non-transitory computer readable medium of claim 13, wherein the at least one criterion comprises one or both of:

a densest valid sample region in the renal cortex; and a densest valid sample region in the liver, wherein the densest valid sample region in the liver is identified based at least in part on one or more of:

a shortest distance to a center line of transducer data;

a shortest distance to the densest valid sample region in the renal cortex;

the densest valid sample region in the liver being at a same image depth as the densest valid sample region in the renal cortex; and the densest valid sample region in the liver being at a same geometrical depth as the densest valid sample region in the renal cortex.

18. The non-transitory computer readable medium of claim 13, wherein:

determining the HRI is based on a ratio of an average of liver data in the liver region of interest and an average of renal cortex data in the renal cortex region of interest, and the liver data and the renal cortex data is one of:

beamformed data, in-phase and quadrature (I/Q) data, post-processed data, and grayscale values.

\* \* \* \* \*